United States Patent
Guenaltay et al.

(10) Patent No.: US 8,410,307 B2
(45) Date of Patent: Apr. 2, 2013

(54) METHOD FOR PRODUCING VINYL ACETATE

(75) Inventors: Mehmet Guenaltay, Emmerting (DE); Willibald Dafinger, Röhrnbach (DE); Peter Holl, Emmerting (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/574,493

(22) PCT Filed: Jan. 14, 2011

(86) PCT No.: PCT/EP2011/050452
§ 371 (c)(1),
(2), (4) Date: Aug. 14, 2012

(87) PCT Pub. No.: WO2011/089070
PCT Pub. Date: Jul. 28, 2011

(65) Prior Publication Data
US 2012/0310007 A1    Dec. 6, 2012

(30) Foreign Application Priority Data
Jan. 21, 2010  (DE) .......................... 10 2010 001 097

(51) Int. Cl.
*C07C 67/54* (2006.01)
*C07C 67/05* (2006.01)
(52) U.S. Cl. ........................................ 560/248; 560/261
(58) Field of Classification Search .......................... None
See application file for complete search history.

(56) References Cited

U.S. PATENT DOCUMENTS

| | | | |
|---|---|---|---|
| 3,438,870 A | 4/1969 | Roscher et al. | |
| 3,458,406 A | 7/1969 | Fisher et al. | |
| 3,692,636 A | 9/1972 | Huguet | |
| 3,738,915 A | 6/1973 | Di Fiore et al. | |
| 3,905,875 A | 9/1975 | Kronig et al. | |
| 4,156,632 A | 5/1979 | Roscher et al. | |
| 4,353,783 A | 10/1982 | Roscher et al. | |
| 4,818,347 A | 4/1989 | Roscher et al. | |
| 4,934,519 A | 6/1990 | Wolf et al. | |
| 5,066,365 A | 11/1991 | Roscher et al. | |
| 6,228,226 B1 | 5/2001 | Hess et al. | |
| 2007/0032678 A1* | 2/2007 | Stamm et al. | 560/248 |

FOREIGN PATENT DOCUMENTS

| | | |
|---|---|---|
| DE | 1282014 | 1/1967 |
| DE | 1668063 | 12/1970 |
| DE | 1618240 | 4/1971 |
| DE | 1768412 | 9/1971 |
| DE | 2132362 | 1/1972 |
| DE | 2610624 | 9/1977 |
| DE | 2945913 | 11/1979 |
| DE | 2943985 | 5/1981 |
| DE | 3422575 | 12/1985 |
| DE | 3934614 | 4/1991 |
| DE | 102005036930 | 2/2007 |
| DE | 102006038689 | 2/2008 |
| EP | 1760065 | 7/2006 |
| WO | WO2008/019873 | 2/2008 |

* cited by examiner

*Primary Examiner* — Paul A Zucker
(74) *Attorney, Agent, or Firm* — RatnerPrestia

(57) ABSTRACT

A method for producing vinyl acetate in a heterogeneously catalyzed, continuous gas phase process by reacting ethylene with acetic acid and oxygen in a reactor and separating the product gas stream substantially comprising ethylene, vinyl acetate, acetic acid, water, carbon dioxide and inert gases.

8 Claims, 1 Drawing Sheet

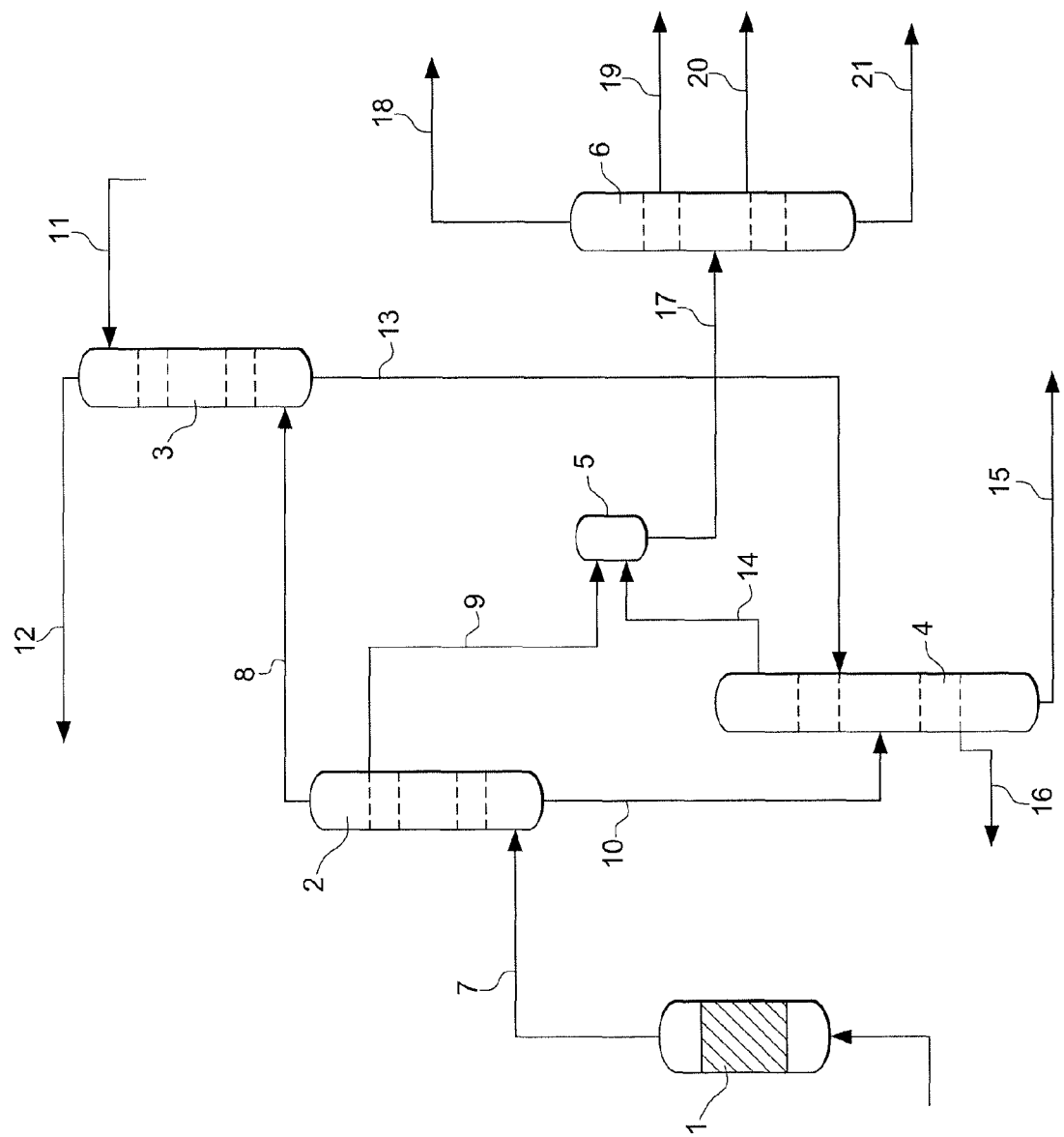

METHOD FOR PRODUCING VINYL ACETATE

CROSS REFERENCE TO RELATED APPLICATIONS

This application is the national phase filing of international patent application No. PCT/EP2011/050452, filed 14 Jan. 2011, and claims priority of German patent application number 10 2010 001 097.9, filed 21 Jan. 2010, the entireties of which applications are incorporated herein by reference.

FIELD OF THE INVENTION

The invention relates to processes for preparing vinyl acetate in a heterogeneously catalyzed, continuous gas-phase process by reacting ethylene with acetic acid and oxygen, in which the work-up of the product stream obtained is more efficient.

BACKGROUND OF THE INVENTION

The preparation of vinyl acetate by reacting ethylene with acetic acid and oxygen or oxygen-containing gases in the gas phase over a fixed-bed catalyst has been known for a long time. The starting materials are reacted in an exothermic reaction, generally at a pressure of from 1 to 30 bar and at a temperature of from 130° C. to 200° C., in a fixed-bed tube reactor or fluidized-bed reactor to form vinyl acetate according to the following overall equation:

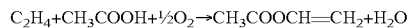

$C_2H_4 + CH_3COOH + \frac{1}{2}O_2 \rightarrow CH_3COOCH=CH_2 + H_2O$

The product gas stream leaving the reactor contains vinyl acetate together with essentially unreacted starting materials, water and also inerts and by-products such as carbon dioxide, acetaldehyde, methyl acetate and ethyl acetate. Inerts are essentially nitrogen, argon, methane and ethane and are introduced into the process as impurities in the starting materials.

To isolate pure vinyl acetate from the product gas stream, many process variants have been proposed. In DE-A 1282014 and DE-A 1668063, it is recommended that the product gas stream be introduced into a first distillation column from which water and low boilers are distilled off at the top and the bottoms are transferred to a second distillation column from which pure vinyl acetate is distilled off at the top. To separate methyl acetate and ethyl acetate from mixtures with vinyl acetate, DE-A 1618240 recommends water-operated extraction processes. U.S. Pat. No. 3,692,636, U.S. Pat. No. 4,934,519 and U.S. Pat. No. 6,228,226 describe azeotropic distillations of mixtures containing vinyl acetate, water, ethyl acetate and acetic acid.

In the process of DE-A 1768412, condensable constituents such as vinyl acetate, acetic acid and water are condensed out from the product gas stream and are introduced as condensates into a first distillation column (azeotropic column) from which vinyl acetate and water are distilled off at the top and are subsequently subjected to a phase separation. The phase containing vinyl acetate is introduced into a second distillation column (dewatering column), the bottoms from which are transferred to a third distillation column (pure vinyl acetate column) from which pure vinyl acetate is obtained at the top. In addition to the abovementioned process steps, the gas phase remaining after condensation of the product gas stream is scrubbed with acetic acid (recycle gas scrubber) in the processes of DE-A 2945913 and DE-A 2943985; the scrubbing solution obtained is introduced into the azeotropic column.

To achieve energy-saving removal of water, DE-A 2610624 recommends introducing the product gas stream into a preliminary dewatering column from which water and vinyl acetate are distilled off at the top and are separated after condensation and phase separation. The phase containing vinyl acetate obtained in this way is recirculated to the preliminary dewatering column or introduced together with the bottoms from the preliminary dewatering column into a dewatering column, the bottoms from which are subjected to further distillative purification steps to obtain pure vinyl acetate. In the processes of EP-A 1760065, DE-A 102006038689, DE 3934614, DE 3422575 and U.S. Pat. No. 4,818,347, the above-described preliminary dewatering column is combined with a recycle gas scrubber operated using acetic acid, an azeotropic column and a dewatering column and also a pure vinyl acetate column, with the pure vinyl acetate being obtained from the top of the latter column.

SUMMARY OF THE INVENTION

In the light of this background, it was an object of the invention to make the processes for isolating vinyl acetate from the product gas stream more efficient, in particular in respect of the use of energy or plant components.

This object has surprisingly been achieved essentially by purifying the product gas stream by means of a preliminary dewatering column, a recycle gas scrubber operated using acetic acid, an azeotropic column and a dewatering column, with the pure vinyl acetate being obtained from the side offtake of the dewatering column. In contrast to the prior art known hitherto, the process of the invention advantageously requires no additional pure vinyl acetate column from which the pure vinyl acetate is conventionally distilled off at the top.

BRIEF DESCRIPTION OF THE DRAWING

FIG. 1 is a schematic flow diagram for a process according to the invention.

DETAILED DESCRIPTION OF THE INVENTION

The invention provides a process for preparing vinyl acetate in a heterogeneously catalyzed, continuous gas-phase process by reacting ethylene with acetic acid and oxygen in a reactor and fractionating the product gas stream containing essentially ethylene, vinyl acetate, acetic acid, water, carbon dioxide and inert gases, by a) introducing the product gas stream into a first distillation column (preliminary dewatering column), b) cooling the gas mixture exiting at the top of the first distillation column to from −20 to +50° C., with the condensate obtained forming an aqueous phase and an organic phase, c) taking off the aqueous phase formed in step b), d) introducing all or part of the organic phase formed in step b) into a collection vessel or feeding it as runback to the top of the first distillation column in step a), e) scrubbing the gas which has not been condensed in step b) in a scrubbing column (recycle gas scrubber) operated using acetic acid and taking off an acetic acid solution containing vinyl acetate at the bottom of the scrubbing column, f) introducing the acetic acid solution containing vinyl acetate from step e) into a second distillation column (azeotropic column), g) introducing the bottom product from step a) likewise into the second distillation column f), h) cooling the overhead vapour from the second distillation column to form an aqueous phase and an organic phase, i) taking off the aqueous phase formed in step h), j) optionally recirculating part of the organic phase formed in step h) as runback to the top of the second distillation column f), k) introducing the remaining part of the organic phase formed in step h) into the collection vessel named in step d), l) introducing the liquid from the collection vessel named in steps k) and d) into a third distillation column (dewatering column), characterized in that m) vinyl acetate is separated off as side offtake stream from the third distillation column of step 1).

FIG. 1 shows a simplified flow diagram for the process of the invention.

The continuous preparation of vinyl acetate is preferably carried out in tube reactors which are charged with a fixed-bed catalyst. These catalysts are generally supported catalysts doped with noble metal (salt)s and promoters, for example, bentonite spheres doped with palladium and with gold and potassium salts. The reactor (1) is supplied with ethylene, oxygen and acetic acid and the reaction is carried out at a pressure of preferably from 8 to 12 bar abs. (recycle gas pressure) and a temperature of preferably from 130 to 200° C.

The product gas stream (7) leaving the reactor (1) contains essentially vinyl acetate, ethylene, acetic acid, water, oxygen and by-products, such as carbon dioxide and ethyl acetate, and also inerts, such as nitrogen, argon, methane and ethane. The product gas stream (7) is preferably introduced directly, if appropriate after being brought to a temperature of from 115 to 130° C., into the first distillation column (preliminary dewatering column) (2) (step a)). The preliminary dewatering column (2) is preferably operated under recycle gas pressure. This is advantageous for energy reasons since the product gas stream (7) contains considerable amounts of ethylene which can in this way be recirculated to the reactor (1) with the smallest possible outlay for decompression and compression. The operating temperature and the runback of the preliminary dewatering column (2) are preferably selected so that virtually the entire ethyl acetate in the product gas stream (7) is collected at the bottom of the preliminary dewatering column (2). The operating temperature at the bottom of the preliminary dewatering column (2) is preferably from 100 to 120° C.

The organic phase (9) formed in step b) usually contains from 90 to 99% by weight, in particular from 95 to 98% by weight of vinyl acetate, $\leq 3\%$ by weight of acetaldehyde, from 0.5 to 8% by weight, in particular from 1 to 2% by weight of water, $\leq 250$ ppm of ethyl acetate and $\leq 250$ ppm of methyl acetate, where the values in % by weight are based on the total weight of the organic phase from step b) (9). The organic phase from step b) (9) thus contains essentially no acetic acid, i.e. preferably $\leq 15$ ppm, particularly preferably $\leq 10$ ppm and at most preferably $\leq 5$ ppm of acetic acid.

The gas (8) which has not been condensed in step b) consists essentially of ethylene and $CO_2$ and small amounts of vinyl acetate and is freed of condensable components in the recycle gas scrubber (3) operated using acetic acid (11) (step e)). The operation of recycle gas scrubbers is known per se to those skilled in the art. The recycle gas stream (12) taken off at the top of the recycle gas scrubber (3) is generally recirculated in its entirety or in part, optionally after purification or compression steps, as recycle gas to the reactor (1). An acetic acid solution containing vinyl acetate collects at the bottom of the recycle gas scrubber (3) from which part or preferably all (13) of a stream is introduced into a second distillation column (azeotropic column) (4) (step f)).

In the region of the top of the azeotropic column (4), the pressure is usually from 1.1 to 1.5 bar abs. and the temperature is from 50 to 90° C. The organic phase (14) formed in step h) usually contains from 90 to 99% by weight, in particular from 95 to 98% by weight, of vinyl acetate, $\leq 3\%$ by weight of acetaldehyde, from 0.5 to 8% by weight, in particular from 1 to 2% by weight, of water, $\leq 250$ ppm of ethyl acetate and $\leq 250$ ppm of methyl acetate, where the values in % by weight are based on the total weight of the organic phase from step h) (14). The organic phase from step h) (14) thus generally contains essentially no acetic acid, i.e. preferably $\leq 15$ ppm, particularly preferably $\leq 10$ ppm and most preferably $\leq 15$ ppm of acetic acid.

A side stream (16) containing ethyl and/or methyl acetate is usually taken off from an enrichment zone above the bottom of the azeotropic column (4). As an alternative, ethyl acetate and/or methyl acetate can also be taken off at the bottom (15) of the azeotropic column (4) and distilled off in a separate distillation column. The bottoms (15) from the azeotropic column (4) contain essentially acetic acid and are preferably recirculated in their entirety or in part to the recycle gas scrubber (3) in step e) as stream (11) or, optionally after further purification, to the reactor (1).

The organic phases (9) and (14) collected in the steps d) and k) carried out together in the collection vessel (5) preferably contain $\leq 25$ ppm, particularly preferably $\leq 10$ ppm and most preferably $\leq 5$ ppm, of acetic acid.

In the region of the top of the dewatering column (6) the pressure is usually from 1.1 to 2 bar abs. and the temperature is from 50 to 90° C., in particular from 70 to 80° C.

It is important in the process of the invention that the purified vinyl acetate is taken off in the stripping section (20) of the dewatering column (6) preferably between the fifth and twentieth plate above the bottom of the dewatering column (6). The vinyl acetate can here be taken off in the form of a gas or in liquid form from the dewatering column (6), depending on the plate of the dewatering column at which the side offtake stream (20) is taken off. In the form of a gas, vinyl acetate is preferably taken off from the fifth to fifteenth plate of the dewatering column (6). If an inhibitor is present in the distillation, the side offtake stream of vinyl acetate (20) is preferably taken off in the form of a gas from the dewatering column (6). Inhibitors are usually used to avoid polymerization. Customary inhibitors are, for example, quinones.

The product obtained in step m) preferably contains $\geq 99\%$ by weight, particularly preferably $\geq 99.5\%$ by weight and most preferably $\geq 99.95\%$ by weight of vinyl acetate, in each case based on the total mass of the product. Furthermore, the product obtained in step m) can contain, for example, $\leq 100$ ppm of water, $\leq 50$ ppm of acetic acid, $\leq 300$ ppm of ethyl acetate or $\leq 50$ ppm of aldehydes, such as acetaldehyde, as secondary components. The Hazen number is $\leq 10$ (determined in accordance with DIN 55945 using a spectrophotometer). The Hazen number is a conventional measure of the colour of transparent substances.

Acetic acid can be formed to a small extent by hydrolysis of vinyl acetate during the distillation in the dewatering column (6). However, it can be ensured by taking off vinyl acetate from the side offtake (20) of the dewatering column (6) that the vinyl acetate isolated contains essentially no acetic acid. The vinyl acetate prepared according to the invention preferably contains $\leq 50$ ppm, particularly preferably $\leq 25$ ppm and most preferably $\leq 5$ ppm, of acetic acid.

The vinyl acetate prepared by the process of the invention is present in the purity required for industrial applications, and this surprisingly despite the fact that an additional pure vinyl acetate column from which vinyl acetate is distilled off at the top in the prior art is not used downstream of the dewatering column as is customary in the previous prior art. For this reason, the process of the invention allows the distillation plant for the pure vinyl acetate column and the associated outlays for maintenance and operation thereof, e.g. energy and steam, to be saved compared to the prior art. This leads to a considerable reduction in the capital and operating costs.

The following example serves to illustrate the invention further, without the invention being restricted in any way:

In a plant as shown in FIG. 1, an organic phase having the following composition: 96 parts by weight of vinyl acetate, 2.4 parts by weight of acetaldehyde, 1.6 parts by weight of water and from 250 to 300 ppm of each of ethyl acetate and methyl acetate was collected in the collection vessel (5) in the manner and under the conditions described above. This organic phase (17) was introduced into the dewatering column (6). The low boilers and the water were separated off in the enrichment section (18) and (19), respectively. Above the bottom but below (18) and (19), a side stream (20) was taken off. The side stream (20) comprised 99.998% by weight of vinyl acetate and contained traces of ethyl acetate (200 ppm), methyl acetate (150 ppm) and acetic acid (30 ppm).

The total mass flow of the bottom offtake stream (21) was 0.5% of the mass flow of the feed (17); the bottom offtake stream was recirculated to the azeotropic distillation.

The invention claimed is:

1. A process for preparing vinyl acetate in a heterogeneously catalyzed, continuous gas-phase process by reacting ethylene with acetic acid and oxygen in a reactor and fractionating the product gas stream containing essentially ethylene, vinyl acetate, acetic acid, water, carbon dioxide and inert gases, by
    a) introducing the product gas stream into a first distillation column (preliminary dewatering column),
    b) cooling the gas mixture exiting at the top of the first distillation column to from −20 to +50° C., with the condensate obtained forming an aqueous phase and an organic phase,
    c) taking off the aqueous phase formed in step b),
    d) introducing all or part of the organic phase formed in step b) into a collection vessel or feeding it as runback to the top of the first distillation column in step a),
    e) scrubbing the gas which has not been condensed in step b) in a scrubbing column (recycle gas scrubber) operated using acetic acid and taking off an acetic acid solution containing vinyl acetate at the bottom of the scrubbing column,
    f) introducing the acetic acid solution containing vinyl acetate from step e) into a second distillation column (azeotropic column),
    g) introducing the bottom product from step a) likewise into the second distillation column f),
    h) cooling the overhead vapour from the second distillation column to form an aqueous phase and an organic phase,
    i) taking off the aqueous phase formed in step h),
    j) optionally recirculating part of the organic phase formed in step h) as runback to the top of the second distillation column f),
    k) introducing the remaining part of the organic phase formed in step h) into the collection vessel named in step d),
    l) introducing the liquid from the collection vessel named in steps k) and d) into a third distillation column (dewatering column), wherein
    m) vinyl acetate is separated off as side offtake stream from the third distillation column of step l).

2. The process for preparing vinyl acetate according to claim 1, wherein the organic phase formed in step b) contains from 90 to 99% by weight of vinyl acetate, ≦2% by weight of acetaldehyde, from 0.5 to 8% by weight of water, ≦250 ppm of ethyl acetate and ≦250 ppm of methyl acetate, where the values in % by weight are based on the total weight of the organic phase from step b).

3. The process for preparing vinyl acetate according to claim 1, wherein the organic phase formed in step h) contains from 90 to 99% by weight of vinyl acetate, ≦2% by weight of acetaldehyde, from 0.5 to 8% by weight of water, ≦250 ppm of ethyl acetate and ≦250 ppm of methyl acetate, where the values in % by weight are based on the total weight of the organic phase from step h).

4. The process for preparing vinyl acetate according to claim 1, wherein the organic phases collected in the collection vessel from steps d) and k) contain ≦25 ppm of acetic acid.

5. The process for preparing vinyl acetate according to claim 1, wherein the vinyl acetate is taken off in the form of a gas or in liquid form from the third distillation column in step m).

6. The process for preparing vinyl acetate according to claim 1, wherein the product separated off in step m) contains ≧99% by weight of vinyl acetate, based on the total mass of the product.

7. The process for preparing vinyl acetate according to claim 1, wherein the product separated off in step m) contains ≦100 ppm of water, acetic acid, ≦300 ppm of ethyl acetate and ≦50 ppm of aldehydes.

8. The process for preparing vinyl acetate according to claim 1, wherein the product separated off in step m) contains ≦50 ppm of acetic acid.

* * * * *